US009803238B1

(12) United States Patent
Koh et al.

(10) Patent No.: US 9,803,238 B1
(45) Date of Patent: Oct. 31, 2017

(54) METHOD AND APPARATUS FOR PURIFYING NUCLEIC ACIDS AND PERFORMING POLYMERASE CHAIN REACTION ASSAYS USING AN IMMISCIBLE FLUID

(71) Applicant: Sandia Corporation, Albuquerque, NM (US)

(72) Inventors: Chung-Yan Koh, Dublin, CA (US); Yooli Kim Light, Pleasanton, CA (US); Matthew Ernest Piccini, Belmont, CA (US); Anup K. Singh, Danville, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 629 days.

(21) Appl. No.: 14/090,040

(22) Filed: Nov. 26, 2013

(51) Int. Cl.
C12Q 1/68 (2006.01)
(52) U.S. Cl.
CPC .................................. C12Q 1/686 (2013.01)
(58) Field of Classification Search
None
See application file for complete search history.

(56) References Cited

U.S. PATENT DOCUMENTS

| 3,555,284 | A | 1/1971 | Anderson |
| 3,744,974 | A | 7/1973 | Maddox |
| 4,125,375 | A | 11/1978 | Hunter |
| 4,156,570 | A | 5/1979 | Wardlaw |
| 4,656,143 | A | 4/1987 | Baker et al. |
| 4,683,579 | A | 7/1987 | Wardlaw |
| 4,844,818 | A | 7/1989 | Smith |
| 5,279,936 | A | 1/1994 | Vorpahl |
| 5,635,362 | A | 6/1997 | Levine et al. |
| 5,639,428 | A * | 6/1997 | Cottingham ............ B01L 3/502 422/105 |
| 5,705,628 | A | 1/1998 | Hawkins |
| 5,882,903 | A | 3/1999 | Andrevski et al. |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 7,033,747 | B2 | 4/2006 | Gordon |
| 7,157,049 | B2 | 1/2007 | Valencia et al. |
| 7,332,326 | B1 | 2/2008 | Kellogg et al. |
| 7,758,810 | B2 | 7/2010 | Lee et al. |
| 2001/0055812 | A1 | 12/2001 | Mian et al. |
| 2002/0098535 | A1 | 7/2002 | Wang et al. |
| 2002/0137068 | A1 | 9/2002 | Haugland et al. |
| 2002/0151043 | A1 | 10/2002 | Gordon |
| 2002/0164659 | A1 | 11/2002 | Rao et al. |
| 2003/0124719 | A1 | 7/2003 | Woodside |
| 2004/0072278 | A1 | 4/2004 | Chou et al. |
| 2005/0186685 | A1 | 8/2005 | Kange et al. |
| 2005/0215410 | A1 | 9/2005 | Merino et al. |
| 2005/0282220 | A1 | 12/2005 | Prober et al. |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1 | 12/2009 | Hinnah et al. |
| 2010/0068754 | A1 | 3/2010 | Kirakossian |
| 2010/0120596 | A1 | 5/2010 | Froman et al. |
| 2010/0151560 | A1 | 6/2010 | Wo et al. |
| 2011/0045958 | A1 | 2/2011 | Pedrazzini |
| 2013/0260447 | A1 * | 10/2013 | Link ........................ G01N 1/38 435/287.2 |
| 2014/0273241 | A1 | 9/2014 | Ochranek et al. |

FOREIGN PATENT DOCUMENTS

| WO | WO-2008/143578 | 11/2008 |
| WO | WO-2009/098237 | 8/2009 |

OTHER PUBLICATIONS

Riahi et al. Analytical Chemistry. 2011. 83(16): 6349-6354 and Supporting Information.
Melting Temperature Calculation. Retrieved on asf from the Internet: http://www.biophp.org/minitools/melting_temperature/demo. php?primer=CGT+TAC+CCG+CAG&basic-1&NearestNeighbor=1&cp=200&cs=50&cmg=0.
Berlier et al. The Journal of Histochemistry and Cytochemistry. 2003. 51(12): 1699-1712.
McBain et al., Polyethyleneimine functionalized iron oxide nanoparticles as agents for DNA delivery and transfection, Journal of Materials Chemistry, 17, pp. 2561-2565, available online Apr. 13, 2007.
PubChem Search results for "2,3-dihydroxypropyl octanoate". Retrieved on Oct. 5, 2016 from the Internet: https://www.ncbi_nim.nih.gov/pccompound/?term=2%2C3-dihydroxypropyl+octanoate. (4 pp.).
PubChem entry for TWEEN 20. Retrieved on Oct. 4, 2016 from the Internet: https://pubchem.ncbi.nlm.nih.gov/compound/Tween_20#section=Names-and-identifiers. (2 pp.).
Sigma-Aldrich product page for Tween 20 archived from Jun. 28, 2012. Retrieved on Oct. 5, 2016 from the Internet: https://web.archive.org/web/20120628080753/http://www.sigmaaldrich.com/catalog.product/sial/p1379?ang=en&region=. (43 pp.).
Abi-Samra, Kameel et al., "Infrared controlled waxes for liquid handling and storage on a CD-microfluidic platform", The Royal Society of Chemistry; Lab on a Chip, 2011, 723-726.
Ahanotu, et al., "Staphylococcal Enterotoxin B as a Biological Weapon: Recognition, Management, and Surveillance of Staphylococcal Enterotoxin", Applied Biosafety; vol. 11 (3), 2006, 120-126.
Albrecht, J.W. et al., "Micro Free-Flow IEF Enhanced Active Cooling and Functionalized Gels", Electrophoresis, 2006, pp. 4960-4969, vol. 27.

(Continued)

Primary Examiner — Stephanie K Mummert
(74) Attorney, Agent, or Firm — Helen S. Baca

(57) ABSTRACT

Embodiments of the present invention are directed toward devices, systems, and methods for purifying nucleic acids to conduct polymerase chain reaction (PCR) assays. In one example, a method includes generating complexes of silica beads and nucleic acids in a lysis buffer, transporting the complexes through an immiscible fluid to remove interfering compounds from the complexes, further transporting the complexes into a density medium containing components required for PCR where the nucleic acids disassociate from the silica beads, and thermocycling the contents of the density medium to achieve PCR. Signal may be detected from labeling agents in the components required for PCR.

20 Claims, 8 Drawing Sheets

(56) References Cited

OTHER PUBLICATIONS

Amersham, "Percoll: Methodology and Applications", 2001, 1-84.
Amukele, et al., "Ricin A-chain activity on stem-loop and unstructured DNA substrates.", Biochemistry; vol. 44(11), Mar. 25, 2005, 4416-4425.
Andersson, et al., "Parallel nanoliter microfluidic analysis system", Clinical Chemistry, 2007.
Baldwin, Robert L. , "How Hofmeister Ion Interactions Affect Protein Stability", Biophysical Journal; vol. 71, Oct. 1996, 2056-2063.
Berry, Scott M., "One-step Purification of Nucleic Acid for Gene Expression Analysis via Immiscible Filtration Assisted by Surface Tension", Lap Chip, May 21, 2011.
Boyko, Matthew et al., "Cell-Free DNA—a Marker to Predict Ischemic Brain Damage in a Rat Stroke Experimental Model", Journal of Neurosurg Anesthesiol, vol. 23, No. 3, Jul. 2011, 222-228.
Brigotti, et al., "Shiga toxin 1 acting on DNA in vitro is a heat-stable enzyme not requiring proteolytic activation", Biochimie Journal; 86(45), 2004, 305-309.
Carney, J. , "Rapid Diagnostic Tests Employing Latex Particles", Analytical Proceedins, Apr. 1990, 99-100.
Curtis, R. A. et al., "A Molecular approach to bioseparations: Protein-protein and protein-salt interactions", Chemical Engineering Science; vol. 61, 2006, 907-923.
Czeiger, David et al., "Measurement of Circulating Cell-Free DNA Levels by a New Simple Fluorescent Test in Patients With Primary Colorectal Cancer", Am J Clin Pathol, 2011, 264-270.
Endo, et al., "RNA N-Glycosidase Activity of Ricin A-chain. Mechanism of Action of the Toxic Lectin Ricin on Eukaryotic Ribosomes", the Journal of Biological Chemistry, vol. 262, No. 17, Jun. 15, 1987, 8128-8130.
Glorikian, Harry et al., "Smart-consumables product development: Implications for molecular diagnostics", DX Direction, 2010, 12-16.
Glorikian, H. et al., "Overview of Microfluidic Applications in IVDS", DX Direction 1, pp. 12-16 (2010).
Goldshtein, Hagit et al., "A Rapid Direct Fluorescent Assay for Cell-Free DNA Quantification in Biological Fluids", Annals of Clinical Biochemistry, 2009, 488-494.
Gorkin, et al., "Centrifugal microfluidics for biomedical applications", www.rsc.org/loc; Lab on a Chip, May 2010, 1758-1773.
Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.
Holmes, David et al., "Leukocyte analysis and differentiation using high speed microfluidic single cell impedance cytometry", Lab on a Chip 9, Aug. 7, 2009, 2881-2889.
Huang, et al., "The Primary Structure of Staphylococcal Enterotoxin B. III. The Cyanogen Bromide Peptides of Reduced and Aminoethylated Enterotoxin B, and the Complete Amino Acid Sequence.", The Journal of Biological Chemistry vol. 245 No. 14, Jul. 25, 1970, 3518-3525.
International Search Report and Written Opinion dated Jun. 28, 2013 for PCT/US2013/032349.
Lee, et al., "Fully integrated lab-on-a-disc for simultaneous analysis of biochemistry and immunoassay from whole blood", Lab Chip, 2011.

Lee, B. S. et al., "A fully automated immunoassay from whole blood on a disc", Lab on a Chip 9, Mar. 5, 2009, 1548-1555.
Lim, C. T. et al., "Bead-based microfluidic immunoassays: The next generation", Biosensors Bioelectronics 22, Jul. 20, 2006, 1197-1204.
Lo, C.T. et al., "Photopolymerized Diffusion-Defined Polyacrylamide Gradient Gels for On-Chip Protein Sizing", The Royal Society of Chemistry, Lab on a Chip, vol. 8, No. 8, 2008, pp. 1273-1279.
Lo, Y. M. D. et al., "Plasma DNA as a Prognostic Marker in Trauma Patients", Clinical Chemistry 46:3, 2000, 319-323.
Madou, Marc et al., "Lab on a CD", Annual Rev. Biomed Eng 8, May 2006, 601-628.
Maes, Melissa L. et al., "Comparison of Sample Fixation and the use of LDS-751 or anti-CD45 or Leukocyte Identification in Mouse Whole Blood for Flow Cytometry", Journal of Immunological Methods, 319(1-2) Jan. 30, 2007, 79-86.
Min, Junhong et al., "Functional Integration of DNA Purification and Concentration Into a Real Time Micro-PCR Chip", The Royal Society of Chemistry; Lab on a Chip, 2011, 259-265.
Price, Christopher P. et al., "Light-Scattering Immunoassay", Principles and Practice of Immunoassay (Second Edition); Chapter 18, 1997, 445-480.
Rhodes, Andrew et al., "Plasma DNA concentration as a predictor of mortality and sepsis in critically ill patients", Critical Care, 2006, 1-7.
Rider, Todd H. et al., "A B Cell-Based Sensor for Rapid Identification of Pathogens", www.sciencemag.org; Science vol. 301, Jul. 11, 2003, 213-215.
Riegger, L. et al., "Read-out concepts for multiplexed bead-based fluorescence immunoassays on centrifugal microfluidic platforms", Sensors and Actuators A-Physical, 2006, 455-462.
Saukkonen, et al., "Cell-Free Plasma DNA as a Predictor of Outcome in Severe Sepsis and Septic Shock", Clinical Chemistry; vol. 54:6, 2008, 1000-1007.
Schaff, et al., "Whole Blood Immunoassay Based on Centrifugal Bead Sedimentation", Clinical Chemistry Automation and Analytical Techniques 57:5, 2011, 753-761.
Schembri, et al., "Portable Simultaneous Multiple Analyte Whole-Blood Analyzer for Point-of-Care Testing", Clinical Chemistry 38/9, 1992, 1665-1670.
Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer; 19(5), May 15, 1977, 621-626.
Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.
Zhang, L. et al., "A New Biodosimetric Method: Branched DNA-Based Quantitative Detection of B1 DNA in Mouse Plasma", The British Journal of Radiology, vol. 83, Aug. 2010, 694-701.
Ziegler, Annemarie et al., "Circulating DNA: a new diagnostic gold mine?", Cancer Treatment Reviews, vol. 28, 2002, 255-271.
Churchill et al., "Detection of Listeria monocytogenes and the toxin listeriolysin O in food", Journal of Microbiological Methods, 2006; 64:141-170.

* cited by examiner

US 9,803,238 B1

METHOD AND APPARATUS FOR PURIFYING NUCLEIC ACIDS AND PERFORMING POLYMERASE CHAIN REACTION ASSAYS USING AN IMMISCIBLE FLUID

STATEMENT REGARDING RESEARCH & DEVELOPMENT

This invention was developed under Contract DE-AC04-94AL85000 between Sandia Corporation and the U.S. Department of Energy. The U.S. Government has certain rights in the invention.

TECHNICAL FIELD

Embodiments of the invention relate generally to purifying nucleic acids with immiscible fluids and conducting polymerase chain reaction assays.

BACKGROUND

Polymerase chain reaction (PCR) assays are generally used for molecular diagnostics due to the sensitivity and specificity of the assay. PCR is a technique which allows a single copy or piece of DNA to be replicated, amplifying the amount of DNA in a sample to be analyzed. In this manner, even single nucleotide changes can be detected through well-constructed PCR assays. PCR generally involves thermal cycling of a sample, e.g. repeated heating and cooling of the sample, to allow for DNA melting and enzymatic replication. The thermal cycling generally takes place in the presence of PCR reagents. PCR reagents generally include primers (e.g. DNA fragments complementary to a target region of interest) and DNA polymerase.

Systems are available for performing PCR with purified nucleic acid inputs. Non-disk-based microfluidic devices integrating sample preparation with amplification and detection exist. The sample input generally requires purified cell populations from culture, suspended in buffers such as PBS; environmental samples often important for biodefense are unable to be analyzed on the platform. Commercial systems for analysis of clinical samples by PCR on microfluidic systems are available. These systems typically require extensive sample preparation before introduction into the system.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Figure 1:
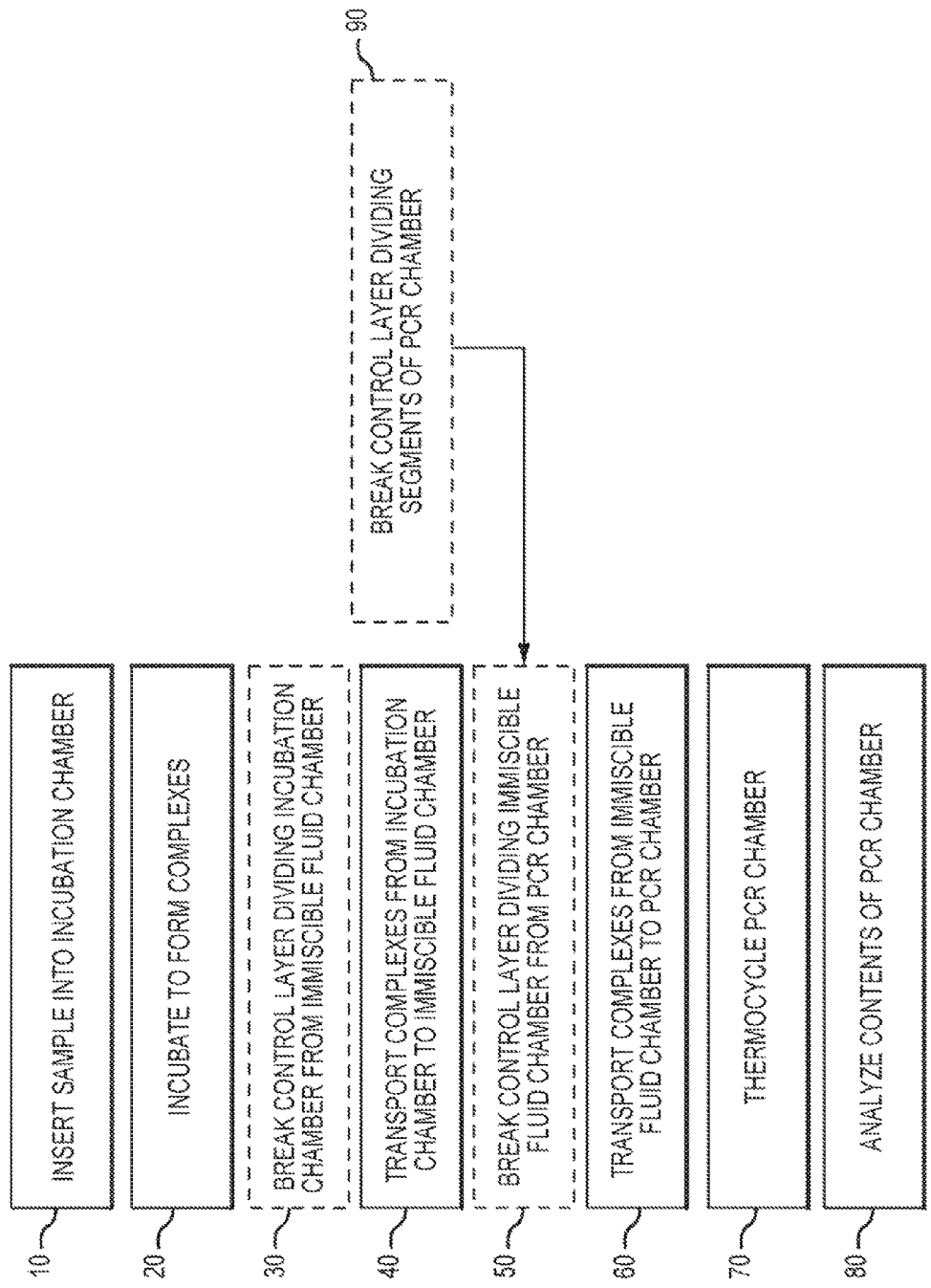
FIG. 1 is a flowchart illustrating a method in accordance with embodiments of the present invention.

FIG. 1 is a flowchart illustrating a method in accordance with embodiments of the present invention. At operation 10, a sample is provided to an incubation chamber with beads and a lysis buffer. The sample may be provided to the incubation chamber in generally any manner used to provide sample to a device. Examples include, but are not limited to, pipetting, injection, or fluid transport including, but not limited to, pressure-driven flow. The incubation chamber may contain beads and a lysis buffer. In some embodiments, the beads and lysis buffer may be provided to the incubation chamber, e.g. using pipetting, injection, or pressure-driven flow, prior to or at the same time as the sample. In other embodiments, the lysis buffer and beads may be pre-loaded in the incubation chamber. A variety of samples may be utilized in accordance with embodiments of the present invention. Generally the sample is a fluid (e.g. a liquid) containing, or which may contain, DNA or DNA fragments which may be amplified using PCR. Samples of interest include, but are not limited to, blood, serum, saliva, and combinations thereof. The sample may be of clinical, environmental, animal, food, water, or other origin. The lysis buffer may be any lysis buffer that is appropriate, or expected to be appropriate, for the sample.

The beads may be macroporous silica microparticles in some examples. These microparticles, through the use of large volumes of porogens during manufacture, may have very large surface area-to-volume ratios. One gram of particles typically has several hundred square meters of surface area. In other embodiments, the beads may have a silica surface which binds to nucleic acids in the presence of high salt. The beads may be polystyrene or have a polystyrene surface that is modified with a surface chemistry which binds nucleic acids in high salt conditions in some examples. A variety of particle sizes may be utilized in accordance with embodiments of the present invention including diameters from 0.5 μm-10 μm, with 5 μm being preferred in some embodiments. Other diameter particles may be used.

Figure 7:
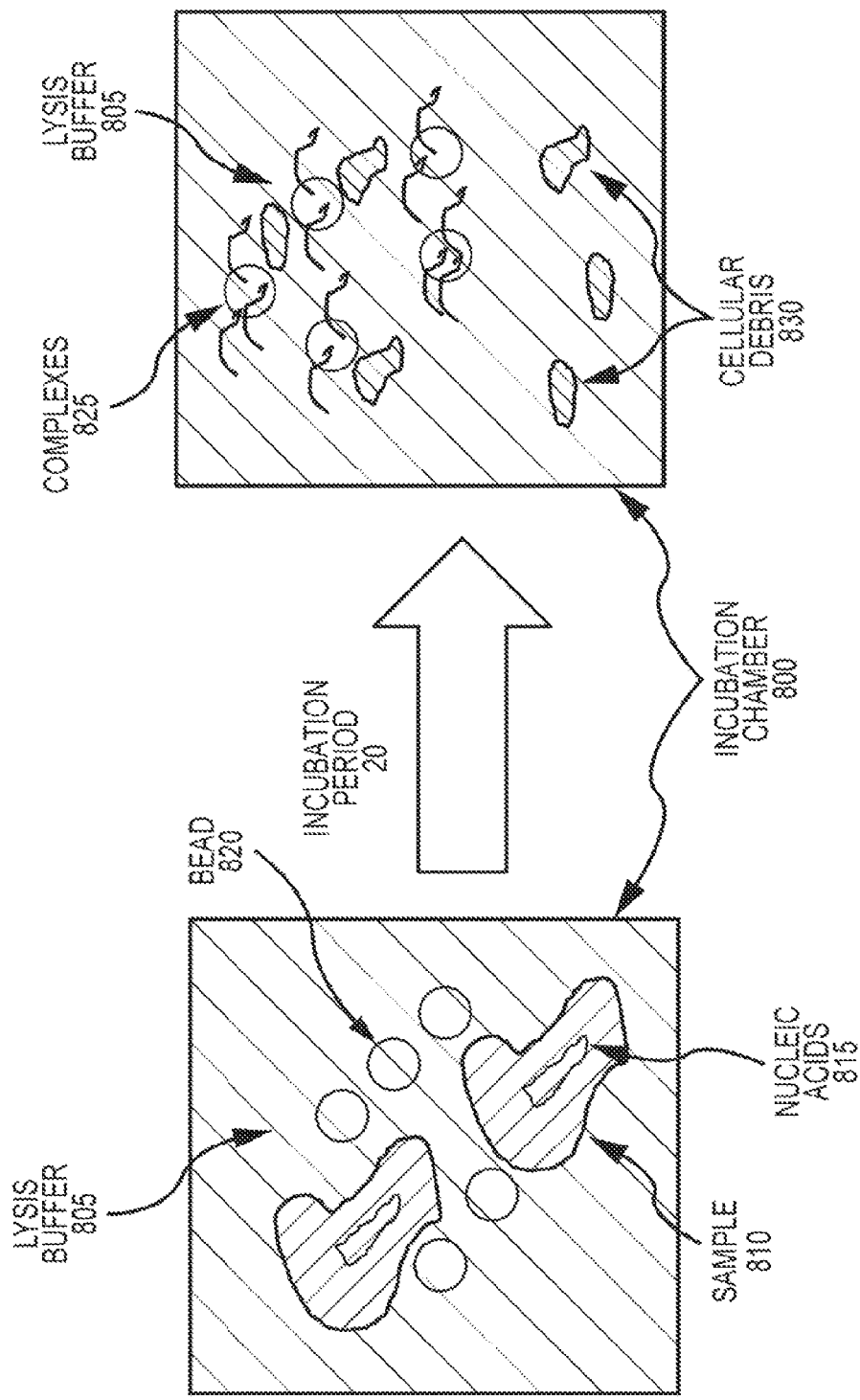
FIG. 7 is a schematic illustration of complex formation in accordance with embodiments of the present invention.

In operation 20, the contents of the incubation chamber are allowed to incubate for a period of time. The period of time is selected to allow for sufficient sample lysis to occur. In some example, the period of time is between 10 and 15 minutes at room temperature. The period of time may vary in accordance with sample type, temperature, quantity, and design of the incubation chamber geometry, for example. FIG. 7 is a schematic illustration of complex formation in accordance with embodiments of the present invention. A sample 810 contains nucleic acids 815 in a lysis buffer 805 with the silica beads 820 in the incubation chamber 800. Under lysis buffer conditions (e.g. high salt) in the incubation chamber, the nucleic acids in the sample may be bound to the silica beads, forming complexes. Accordingly, following incubation 20, cells may be lysed and nucleic acids 815 bound to beads 820, forming complexes 825. In some embodiments, cellular debris 830 may be formed during lysis. In some embodiments, cell lysis may not be required, a lysate buffer may not be used. In some embodiments, nucleic acids may be bound to beads in a sample preparation step not associated with the device in use, and provided directly to a chamber of a device.

In operation 40, complexes are transported from the incubation chamber to a chamber containing an immiscible fluid. A variety of fluid transport mechanisms may be used to effect transport of the complexes including, but not limited to, centrifugal force, gravitational force, electrophoretic transport, or combinations thereof. Optionally, the incubation chamber and immiscible fluid chamber may be separated by a control layer. The control layer may fluidically isolate the incubation chamber from the immiscible fluid chamber (e.g. by forming a barrier between the chambers), and the control layer may be broken during operation 30 when or prior to when transport of the complexes between the chambers is desired. Examples of control layers include, but are not limited to, valves, sacrificial layers, breakable layers (e.g. membranes), or combinations thereof.

Figure 8:
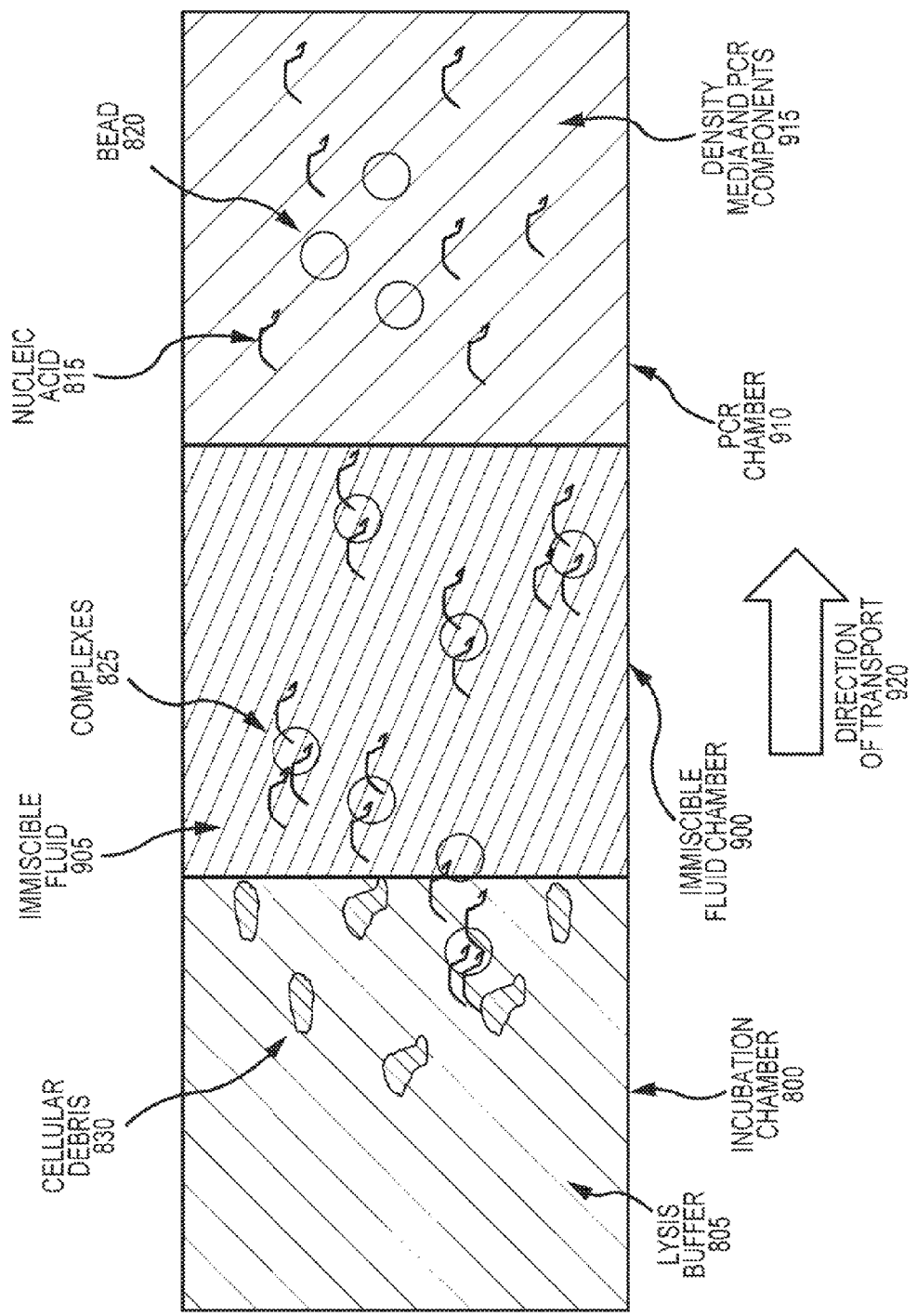
FIG. 8 is a schematic illustration of complex transport in accordance with embodiments of the present invention.

FIG. 8 is a schematic illustration of complex transport in accordance with embodiments of the present invention. The immiscible fluid 905 generally excludes the lysis buffer 805, and/or interfering compounds of the lysis buffer, for example, cellular debris 830, from transport into the immiscible fluid chamber 900 through hydrophobic interactions, and/or a combination of density and hydrophobic interactions. The immiscible fluid chosen may be denser than the cellular debris, the lysis buffer, or combinations thereof. Accordingly, as a centrifugal or gravitational force is applied to a device containing the incubation and immiscible fluid chambers, the cellular debris, lysis buffer, and/or combinations thereof, may be physically excluded from transport into the immiscible fluid chamber due to their density. The beads used to form the complexes 825 may be denser than the immiscible fluid. Accordingly, the beads may be transported through the immiscible fluid responsive to a centrifugal or gravitational force, or combinations thereof. Additionally or instead, the immiscible fluid may contain perfluor-compounds, which may exclude water and/or water-based compounds from the lysis buffer from transport into the immiscible fluid. In this manner, the beads may be washed of interfering compounds and the nucleic acids bound to the beads may be chemically isolated from the lysate and other matrix components, thus providing purified complexes including nucleic acids in the immiscible fluid. Suitable immiscible fluids include, but are not limited to: oil, perfluorohydrocarbons, partially fluorinated hydrocarbons, silicone-based liquids, and immiscible aqueous mixtures, such as a combination of poly(ethylene glycol) and dextran.

The complexes 825 may be transported 920 through the immiscible fluid 905, which may advantageously provide washing and isolation benefits in some examples. The complexes 825 may be transported 920 to a PCR chamber 910 in operation 60, as shown schematically in FIG. 8. Optionally, the immiscible fluid chamber 900 and the PCR chamber 910 can be separated by a control layer (Not shown in FIG. 8). Examples of control layers include, but are not limited to, valves, sacrificial layers, breakable layers (e.g. membranes), or combinations thereof. The control layer generally may provide a fluidic barrier between the immiscible fluid chamber 900 and the PCR chamber 910 but may be broken, opened, or combinations thereof to place the chambers in fluidic communication. The control layer, may be broken or otherwise opened when or prior to when transport of the complexes between the chambers is desired at operation 50.

The PCR chamber generally contains a density medium and PCR reagents (e.g. components necessary for PCR amplification). PCR reagents contained in the density medium may include, but are not limited to, DNA polymerase (such as Taq polymerase), deoxynucleoside triphosphates, magnesium, potassium, DNA template of the product to be amplified, DNA primers, and combinations thereof. In some example methods, the PCR reagents may be provided to the PCR chamber (e.g. by pipetting, injection, or other fluid transport technique). In other examples, the PCR reagents may already be provided in the PCR chamber. The PCR chamber may include a density medium 915, as shown in FIG. 8. The density medium any be an aqueous solution that may be low-salt, allowing nucleic acids 815 to desorb from the surface of the beads 820 for enhanced PCR efficiency in some examples. The density medium may contain Percoll® or iodixanol in some examples. The PCR chamber may be thermocycled as appropriate for the chosen PCR assay in operation 70. Thermocycling may be achieved through the use of generally any heating and/or cooling elements, including but not limited to Peltier thermoelectric elements. After cycles of amplification, labeling agents, which may be provided in the PCR chamber, bind to the amplified product, if present, and the contents of the PCR chamber may be analyzed at operation 80. A variety of labeling agents may be used including those that facilitate optical, electrical, electrophoretic detection, or combinations thereof. Optical methods may include fluorescence, total internal reflection fluorescence (TIRF), turbidimetric, chemiluminescent, or bioluminescence. In one embodiment, an electrical detection method may be through reduction potential measurements. In some examples, the labeling agents may be dyes that may be detected via laser-induced fluorescence. Labeling agents may include SYBR® green, Syto® 9, SYBR® Gold, or other appropriate molecular beacons or probes. In some examples, the labeling agents may intercalate with the amplified product, if present.

In some examples, the PCR chamber may be divided into two segments by a control layer (e.g. a valve, sacrificial, or other breakable layer). The first segment may contain freeze dried or otherwise shelf-stable PCR reagents (e.g. DNA polymerase) and the second segment may contain the density medium. Before the complexes are transported from the immiscible fluid chamber to the PCR chamber, the control layer between the two segments may be broken in operation 90, causing the PCR reagents and the density medium to be combined. In this manner, a shelf-stable device may be provided in some examples which includes the reagents for performing methods described herein, and an end user need only provide the sample into the device. In some examples, the end user need not provide the PCR reagents, lysis buffer, or beads, or combinations thereof. Instead, those components may be provided to the user with (e.g. contained in) the device in some examples.

Figure 2:
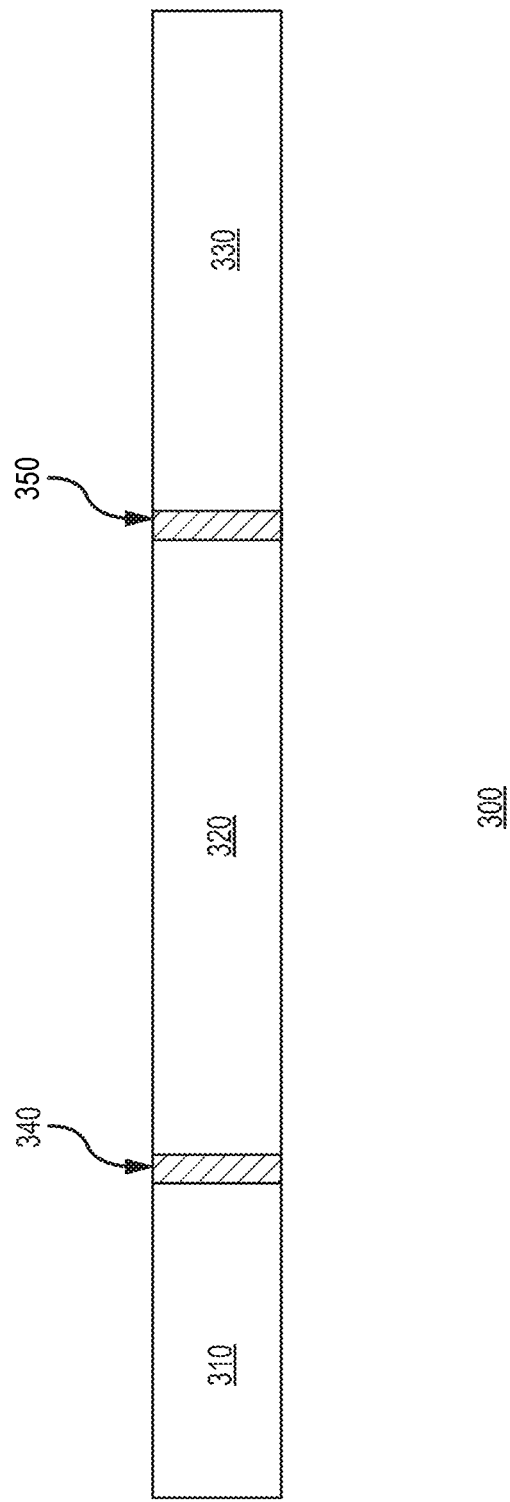
FIG. 2 is a schematic illustration of an apparatus arranged in accordance with embodiments of the present invention.

FIG. 2 is a schematic illustration of an apparatus arranged in accordance with embodiments of the present invention. The chambers 310, 320, and 330 are shown. The chambers may generally be implemented using any arrangement of fluidic features suitable for holding the described components. For example, the chambers may be separate features or may be different segments of a same fluid channel or other structure. The incubation chamber 310 may contain lysis buffer, beads, and sample. The immiscible fluid is contained in chamber 320, and the density medium and PCR components are in chamber 330. The optional control layers (e.g. membranes) are shown at 340 and 350. Chamber 330 may be further divided into two segments, as described above, although not shown in FIG. 2, by another control layer with the freeze dried PCR components in one segment and the density medium in the other segment. Examples of the devices described herein, such as the device 300 of FIG. 2 may be implemented in a microfluidic system. Although not shown in FIG. 2, any number of additional components may also be included in systems described herein including, but not limited to, valves, pumps, inputs, outputs, mixers, heaters, or combinations thereof. The example shown in FIG. 2 is intended to represent a top-down view of a microfluidic device, with the inputs and outputs of a channel containing the chambers 310, 320, and 330 not shown.

Figure 3:
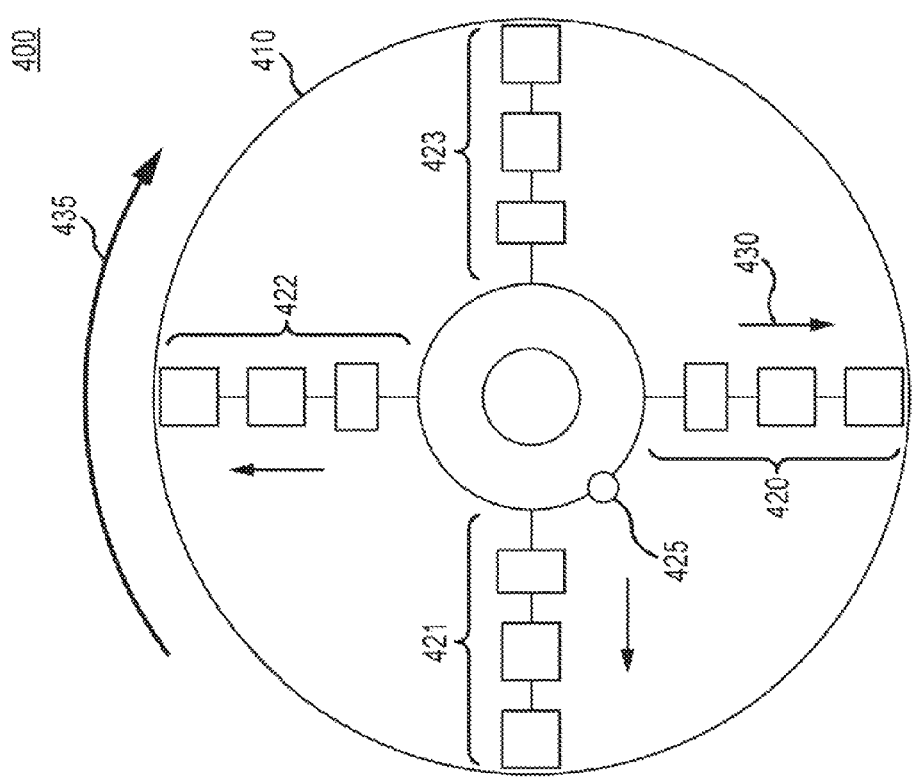
FIG. 3 is a schematic illustration of a microfluidic disk arranged in accordance with embodiments of the present invention.

FIG. 3 is a schematic illustration of a microfluidic disk 400 arranged in accordance with the embodiments of the present invention. The microfluidic disk 400 may include a substrate 410 which may at least partially define regions of assay areas 420-423. The microfluidic disk 400 may include a fluid inlet port 425 in fluid communication with the assay areas 420-423. Each assay area may include any variety of fluidic features and components, including but not limited to, channels, chambers, valves, pumps, etc. As shown in FIG. 3, each assay area includes an incubation chamber, an immiscible fluid chamber, and a PCR chamber. During operation, fluids including sample liquids, density media, and/or beads suspended in a fluid, may be transported using centrifugal force from an interior of the microfluidic disk 400 toward a periphery of the microfluidic disk 400 in a direction indicated by arrow 430. The centrifugal force may be generated by rotating the microfluidic disk 400 in the direction indicated by the arrow 435 or the opposite direction.

The substrate 410 may be implemented by using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the disk 400. In some embodiments, however, opaque plastic, metal, or semiconductor substrates may be used. In some embodiments, multiple materials may be used to implement the substrate 410. The substrate 410 may be made up of multiple layers. The substrate 410 may include surface treatments or other coatings, which may in some embodiments, enhance compatibility with fluids placed on the substrate 410. In some embodiments surface treatments or other coatings may be provided to control fluid interaction with the substrate 410. While shown as a round disk in FIG. 3, the substrate 410 may take substantially any shape, including square.

In some embodiments, the substrate 410 may itself be coupled to a motor for rotation. In some embodiments, the substrate may be mounted on another substrate or base for heating and/or rotation. For example, a microfluidic chip fabricated at least partially in a substrate may be mounted on another substrate for spinning. In some examples, the microfluidic chip may be disposable while the substrate or base it is mounted on may be reusable. In some examples, the entire disk may be disposable. In some examples, a disposable cartridge including one or more microfluidic channels may be inserted into the disk or other mechanical rotor that forms part of a detection system.

The substrate 410 may generally, at least partially, define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 µm or less. In some embodiments, the microfluidic features may have dimensions of around 100 µm or less. Other dimensions may be used the substrate 410 may define one or more fluidic features, including any number of channels, chambers, inlet/outlet ports, or other features.

A fluid inlet port 425 may be provided to receive a fluid that may be analyzed using the microfluidic disk 400. The fluid inlet port 425 may have generally any configuration, and a fluid sample may enter the fluid inlet port 425 utilizing substantially any fluid transport mechanism, including pipetting, pumping, or capillary action. The fluid inlet port 425 may take substantially any shape. Generally, the fluid inlet port 425 is in fluid communication with at least one assay area 420, and may be in fluid communication with multiple assay areas 420-423 in FIG. 3. Generally, by fluid communication it is meant that a fluid may flow from one area to the other, either freely or using one or more transport forces and/or valves, and with or without flowing through intervening structures.

The assay area 420 generally may include one or more channels in fluid communication with the fluid inlet port 425. Although four assay areas 420-423 are shown in FIG. 3, generally any number may be present on the microfluidic disk 400.

As the microfluidic disk 400 is rotated in the direction indicated by the arrow 435 (or in the opposite direction), a centrifugal force may be generated. The centrifugal force may generally transport fluid from the inlet port 425 into one or more of the assay areas 420-423. Accordingly, the microfluidic disk 400 may be used to perform assays described herein.

Figure 4:
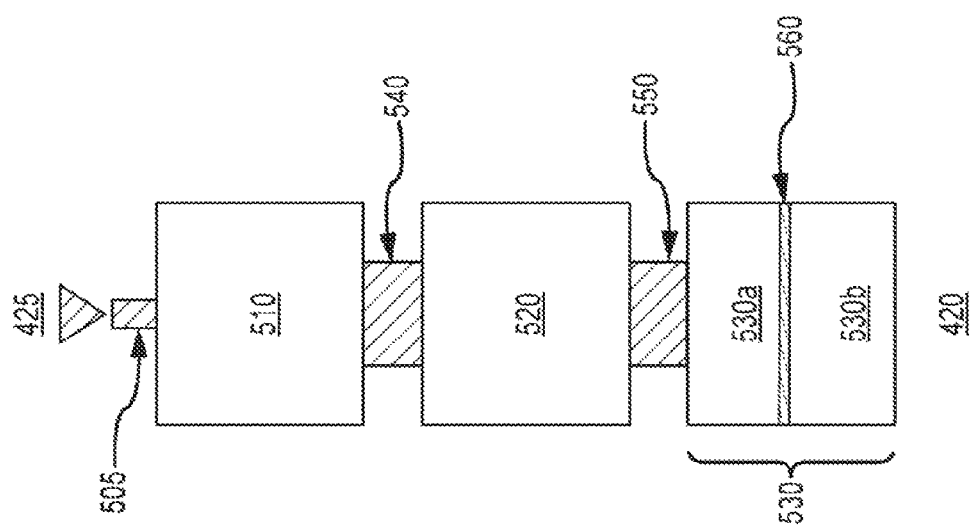
FIG. 4 is a schematic illustration of an apparatus arranged in accordance with embodiments of the present invention.

FIG. 4 is a schematic illustration of an assay area 420 of a microfluidic disk in accordance with an embodiment of the present invention. FIG. 4 provides a top-down view of an assay area. The assay area 420 includes a channel 505 in fluid communication with the fluid inlet port 425. The channel 505 is in fluid communication with an incubation chamber 510. The incubation chamber 510 is in fluid communication to an immiscible fluid chamber 520. The fluid communication may be interrupted by a control layer 540 between the incubation chamber 510 and the immiscible fluid chamber 520. The immiscible fluid chamber 520 is in fluid communication to a PCR chamber 530. The fluid communication may be interrupted by a control layer 550 between the immiscible fluid chamber 520 and the PCR chamber 530. The PCR chamber 530 may be further segmented into two section 530a and 530b in fluid communication with each other. The fluid communication may be interrupted by a control layer 560 between the segments. The control layers may be made of wax in some embodiments of the invention and may be broken by heating, for example. Other types of control layers may be used, including, for example, layers that may be punctured or otherwise broken. For example, plastic or other membranes may be used and a pin or other actuator may be deployed to break the membrane and create fluid communication in some examples. Transport of fluids between chambers 510, 520, and 530 may be achieved through centrifugal forces.

Figure 5:
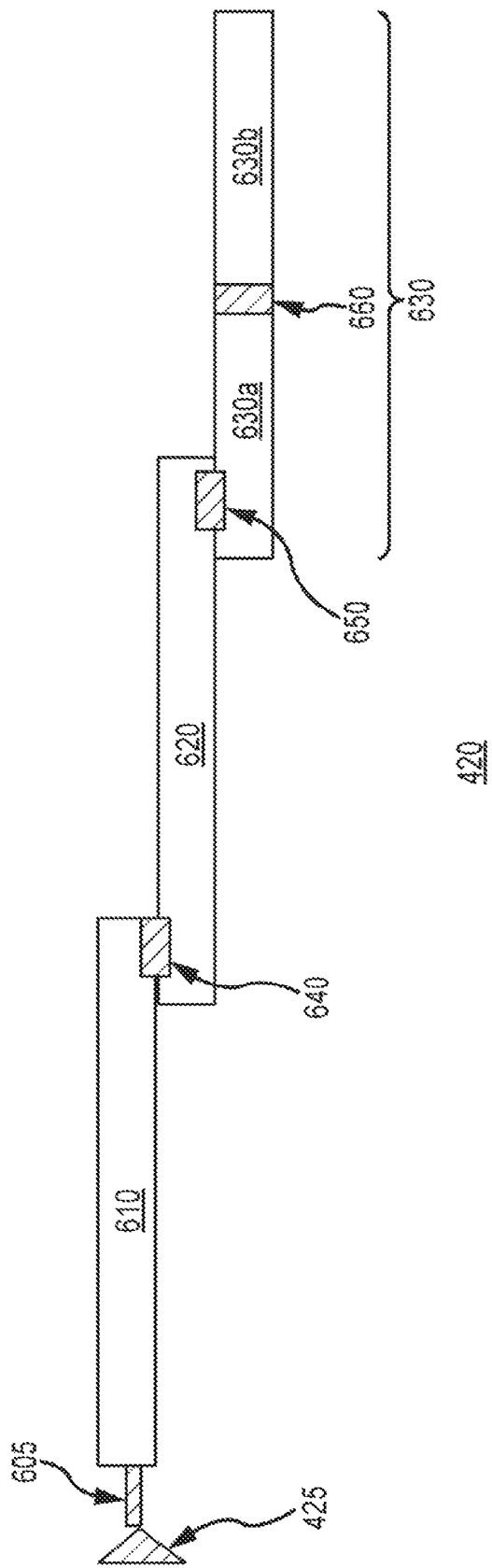
FIG. 5 is a schematic illustration of an apparatus arranged in accordance with embodiments of the present invention.

FIG. 5 is a schematic illustration of an assay area arranged in accordance with embodiments of the present invention. FIG. 5 is a cross-sectional view of an assay area including a channel 605 in fluid communication with the fluid inlet port 425, and may be used to implement the assay area 420 of FIG. 3. In FIG. 5, the bottom surface of the PCR chamber 630 may be near the same level as the bottom surface of the substrate 410. The bottom surface of the immiscible fluid chamber 620 may be within the substrate 410, but above the bottom surface of the PCR chamber 630. The incubation chamber 610 is at least partially defined by the substrate 410, and its bottom surface may be above the level of the immiscible fluid chamber 620. The chambers 610, 620, and 630 may be in fluid communication. Optionally, the fluid communication can be interrupted by control layers 640 and 650. Additionally, the PCR chamber 630 may be further segmented into two segments 630a and 630b in fluid communication with each other. The fluid communication between 630a and 630b may be interrupted by control layer 660.

Figure 6:
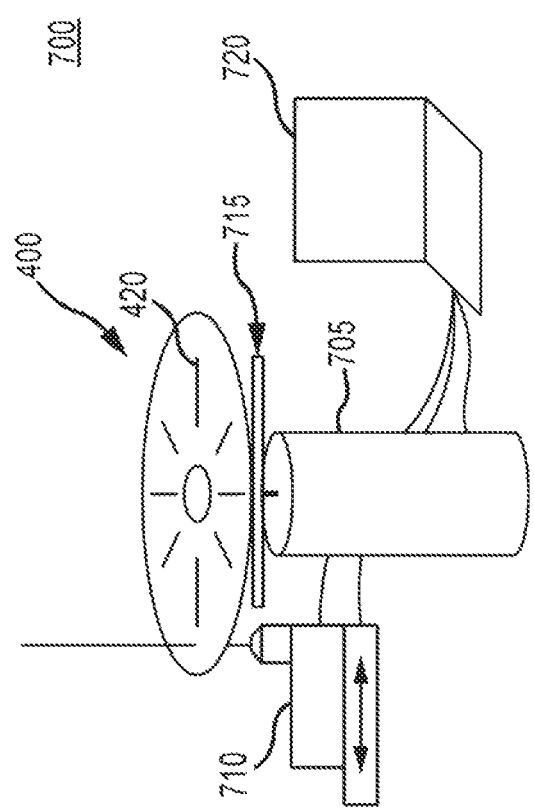
FIG. 6 is a schematic illustration of a system arranged in accordance with embodiments of the present invention.

FIG. 6 is a schematic illustration of a system according to an embodiment of the present invention. The system 700 may include the disk 400 of FIG. 3. with one or more assay areas 420. A motor 705 may be coupled to the disk 400 and configured to spin the disk 400, generating centrifugal forces. A detection module 710 may be positioned to detect signal from labeling agents in a detection region of the assay area 420. A heating element 715 may be positioned between the motor and the disk to heat the disk. A processing device 720 may be coupled to the motor 705, the detection module 710, and the heating element 715 and may provide control signals to those components. The processing device 720 may further receive electronic signals from the detection module 710 corresponding to the labeling agent signals received by the detection module 710. All or selected components shown in FIG. 6. may be housed in a common housing in some examples. Microfluidic disks, which may be disposable, may be placed on the motor of 705 and removed, such that multiple disks may be analyzed by the system 700.

The motor 705 may be implemented using a centrifugation and/or stepper motor. The motor 705 may be positioned relative to the detection module 710 such that, when the disk 400 is situated on the motor 705, the disk is positioned such that a detection region of the assay area 420 is exposed to the detection module 710.

The heating element of 715 may be implemented using a Peltier heating element. The heating element 715 may be positioned relative to the motor 705 such that it may heat the disk 400 both when the motor 705 is spinning the disk 400, and when it is not spinning the disk 400.

The detection module 710 may include a detector suitable for detecting signal from labeling agents in the components for PCR. The detector may include, for example, a laser and optics suitable for optical detection of fluorescence from fluorescent labeling agents. The detection module may include one or more photomultiplier tubes. In other examples, other detectors, such as electronic detectors or CCD cameras, may be used. The detection module may further comprise a detector suitable for measuring the temperature of different portions of the disk. The detector may be implemented with a thermistor or an infrared thermometer.

The processing device 720 may include one or more processing units, such as one or more processors. In some examples, the processing device 720 may include a controller, logic circuitry, and/or software for performing functionalities described herein. The processing device 720 may be coupled to one or more memories, input devices, and/or output devices including, but not limited to, disk drives, keyboards, mice, and displays. The processing device may provide control signals to the motor 705, to rotate the disk 400 at selected speeds for selected times. The processing device may provide control signals to the detection module 710, including one or more detectors and/or actuators, to detect signals from the labeling agents or temperature from different regions of the disk 400. The processing device may develop these control signals in accordance with input from an operator and/or in accordance with software including instructions encoded in one or more memories, where the instructions, when executed by one or more processing units, may cause the processing device to output a predetermined sequence of control signals. The processing device 720 may receive electronic signals from the detection module 710 indicative of the detected signal from labeling agents. The processing device 720 may detect a target product and/or calculate a quantity of a target product in a fluid sample based on the signals received from the detection module 710. Accordingly, the processing device 720 may perform calculations. The calculations may be performed in accordance with software including one or more executable instructions stored on a memory causing the processing device to perform the calculations. Results may be stored in memory, communicated over a network, and/or displayed. It is to be understood that the configuration of the processing device 720 and related components is quite flexible, and any of a variety of computing systems may be used including server systems, desktops, laptops, controllers, and the like.

Accordingly, in some examples the processing device 720 may be configured (e.g. programmed, which may be through the use of executable instructions stored on a computer readable medium) to perform PCR. A user, or another system (e.g. a robotic dispenser), may input a sample into an assay region of the microfluidic disk shown in FIG. 6. The user (or other system) may provide an indication to the processing device 720 that PCR should be implemented. The processing device 720 may provide control signals to implement the method of FIG. 1 in some examples. For example, the processing device 720 may wait a predefined period of time (e.g. an incubation time) before spinning the disk to transport complexes through the immiscible fluid. Optionally, the processing device 720 may provide a control signal to an actuator to disrupt a control layer separating the incubation chamber from the immiscible fluid chamber. For example, the processing device 720 may provide a control signal to a heater to melt a wax control layer between the chambers. In other examples, the processing device 720 may provide a control signal to an actuator positioned to puncture or otherwise break the control layer.

The processing device 720 may provide control signals to spin the disk to transport complexes through the immiscible fluid. The processing device 720 may further provide control signals to spin the disk to transport complexes into the PCR chamber. In some examples, the processing device 720 may provide control signals to melt, puncture, or otherwise disrupt a control layer to create fluid communication between segments of a PCR chamber and/or between the PCR chamber and the immiscible fluid chamber. For example, the processing device 720 may provide a control signal to a heater to melt a wax control layer between the chambers. In other examples, the processing device 720 may provide a control signal to an actuator positioned to puncture or otherwise break the control layer.

The processing device 720 may further provide control signals to a heater and/or cooler to effect thermocycling for performing PCR in the PCR chamber.

In this manner, automated PCR may be conducted by systems and methods described herein. A user (or other system) may apply a sample to a system described herein, indicate that PCR is to be performed, and a processing device, such as the processing device 720 may provide the control signals to spin the disk, heat the disk, and open any relevant control layers in an appropriate sequence to transport bound complexes through an immiscible fluid into a density medium and perform PCR.

From the foregoing it will be appreciated that, although specific embodiments of the invention have been described herein for purposes of illustration, various modifications may be made without deviating from the spirit and scope of the invention.

What is claimed is:

1. An apparatus for conducting an assay, the apparatus comprising:
    a. a first fluidic feature which contains a fluid sample, wherein the fluid sample includes a plurality of complexes, individual ones of the complexes comprising a plurality of nucleic acids and a bead;
    b. a second fluidic feature adjacent to said first fluidic feature, said second fluidic feature containing an immiscible fluid having a density greater than that of said fluid sample but lower than said complexes; and
    c. a third fluidic feature adjacent to said second fluidic feature, which contains a density medium, wherein the density medium contains the components necessary for polymerase chain reaction (PCR) and said density medium has a density greater than said immiscible fluid but lower than said complexes.

2. The apparatus of claim 1, further comprising a first control layer between the first and second fluidic features and a second control layer between the second and third fluidic features, said first and second control layers configured to be broken to create fluid communication between the first and second fluidic features and the second and third fluidic features.

3. The apparatus of claim 1, wherein said fluidic features are portions of the same channel.

4. The apparatus of claim 1, wherein said fluidic features are separate chambers in fluid communication.

5. The apparatus of claim 1, wherein said fluidic features are contained on a microfluidic disk.

6. The apparatus of claim 1, wherein the third fluidic feature comprises a first segment holding freeze dried PCR components and a second segment containing the density media, said first and second segments being separated by a third control layer, said third control layer configured to be broken to create fluid communication between the first and second segments of said third fluidic feature.

7. The apparatus of claim 1, wherein the second fluidic feature's bottom surface is lower than said first fluidic feature's bottom surface and the third fluidic feature's bottom surface is lower than said second fluidic feature's bottom surface.

8. A system for conducting an assay, the system comprising:
    a. an apparatus comprising:
        i. a first fluidic feature which contains a fluid sample, wherein the fluid sample includes a plurality of complexes, individual ones of the complexes comprising a plurality of nucleic acids and a bead;
        ii. a second fluidic feature adjacent to said first fluidic feature, said second fluidic feature containing an immiscible fluid having a density greater than that of said fluid sample but lower than said complexes;
        iii. a third fluidic feature adjacent to said second fluidic feature, which contains a density medium, wherein the density medium contains the components necessary for polymerase chain reaction (PCR) and said density medium has a density greater than said immiscible fluid but lower than said complexes;
    b. a motor coupled to the apparatus, the motor configured to receive a motor control signal and spin the apparatus responsive to the motor control signal;
    c. a heating element in contact with the lower surface of the apparatus, the heating element configured to receive a heater control signal and heat the apparatus responsive to the heater control signal;
    d. a detection module positioned to detect a signal from label agents included in the components necessary for PCR, wherein the detection module is configured to generate an electronic detection signal based, at least in part, on the signal from the label agents; and
    e. a processing device coupled to the motor, the heating element, and the detection module, wherein the processing device is configured to allow an incubation period, generate the motor control signal and provide the motor control signal to the motor, generate the heater control signal and provide the heater control signal to the heating element, and wherein the processing device is further configured to receive the electronic detection signal from the detection module.

9. The system of claim 8, wherein the apparatus further comprises a first control layer between the first and second fluidic features and a second control layer between the second and third fluidic features, said first and second control layers configured to be broken to create fluid communication between the first and second fluidic features and the second and third fluidic features.

10. The system of claim 9, wherein a processing device is further configured to break the control layers by sending a heater control signal to the heating element.

11. The system of claim 10, wherein the third fluidic feature further comprises a first segment holding freeze dried PCR components and a second segment containing the density media, said first and second segments being separated by a third control layer, said third control layer configured to be broken to create fluid communication between the first and second segments of said third fluidic feature.

12. The system of claim 8, wherein said fluidic features are contained on a microfluidic disk.

13. The apparatus of claim 1, wherein said bead has a density greater than that of said immiscible fluid.

14. The apparatus of claim 1, wherein said complexes are configured to be transported through the immiscible fluid by way of centrifugal force.

15. The apparatus of claim 1, wherein said complexes are configured to be transported into the density medium by way of centrifugal force.

16. The apparatus of claim 1, wherein said complexes are configured to be transported through said first fluidic feature to said second fluidic feature by way of centrifugal force.

17. The apparatus of claim 16, wherein said complexes are configured to be transported through said second fluidic feature to said third fluidic feature by way of centrifugal force.

18. The apparatus of claim 1, further configured to effect transport of said complexes through the immiscible fluid and into a density medium by way of centrifugal force arising from spinning the apparatus.

19. The system of claim 8, wherein said complexes are configured to be transported through the immiscible fluid by way of centrifugal force.

20. The system of claim 8, wherein said complexes are configured to be transported into the density medium by way of centrifugal force.

* * * * *